United States Patent
Perez

(10) Patent No.: US 8,435,276 B2
(45) Date of Patent: May 7, 2013

(54) METHOD AND APPARATUS FOR THE COMBINED APPLICATION OF LIGHT THERAPY, OPTIC DIAGNOSIS, AND FLUID TO TISSUE

(76) Inventor: Thomas Perez, Chicago, IL (US)

(*) Notice: Subject to any disclaimer, the term of this patent is extended or adjusted under 35 U.S.C. 154(b) by 890 days.

(21) Appl. No.: 12/428,046

(22) Filed: Apr. 22, 2009

(65) Prior Publication Data

US 2009/0204188 A1    Aug. 13, 2009

Related U.S. Application Data

(63) Continuation-in-part of application No. 11/363,554, filed on Feb. 27, 2006, now abandoned.

(51) Int. Cl.
*A61N 5/08* (2006.01)

(52) U.S. Cl.
USPC ................. 607/94; 600/104; 607/92

(58) Field of Classification Search .......... 600/101–183; 606/2–19; 607/88–94
See application file for complete search history.

(56) References Cited

U.S. PATENT DOCUMENTS

| | | | |
|---|---|---|---|
| 4,538,613 A | | 9/1985 | Rosenberg |
| 4,830,460 A * | | 5/1989 | Goldenberg .................. 385/118 |
| 5,334,207 A | | 8/1994 | Gay, Jr. |
| 5,919,135 A | | 7/1999 | Lemelson |
| 6,113,566 A | | 9/2000 | Schleicher |
| 6,679,835 B2 * | | 1/2004 | Moriyama .................... 600/133 |
| 6,863,650 B1 * | | 3/2005 | Irion ............................ 600/104 |
| 7,901,441 B2 * | | 3/2011 | Graves ........................... 607/88 |
| 2002/0026188 A1 | | 2/2002 | Balbierz et al. |
| 2003/0045916 A1 * | | 3/2003 | Anderson et al. ............... 607/89 |
| 2003/0082105 A1 | | 5/2003 | Fischman et al. |
| 2003/0215180 A1 | | 11/2003 | Dimas et al. |
| 2005/0245789 A1 * | | 11/2005 | Smith et al. ................... 600/159 |
| 2005/0251230 A1 | | 11/2005 | MacKinnon et al. |
| 2005/0279354 A1 | | 12/2005 | Deutsch et al. |
| 2006/0009821 A1 | | 1/2006 | Perez |
| 2006/0085053 A1 * | | 4/2006 | Anderson et al. ............... 607/94 |
| 2006/0276862 A1 | | 12/2006 | Irwin |
| 2007/0156211 A1 | | 7/2007 | Ferren |
| 2007/0162050 A1 | | 7/2007 | Sartor |
| 2007/0213590 A1 * | | 9/2007 | Squicciarini .................. 600/172 |
| 2007/0244524 A1 | | 10/2007 | Qu |
| 2009/0069743 A1 | | 3/2009 | Krishnamoorthy et al. |
| 2009/0156900 A1 * | | 6/2009 | Robertson ..................... 600/160 |
| 2009/0167149 A1 * | | 7/2009 | Ito ................................. 313/501 |

FOREIGN PATENT DOCUMENTS

| | | |
|---|---|---|
| DE | 157667 | 12/1982 |
| WO | 2004064623 | 5/2004 |
| WO | WO 2004098709 | 11/2004 |
| WO | 2008055159 | 8/2008 |

* cited by examiner

*Primary Examiner* — Henry M Johnson, III
(74) *Attorney, Agent, or Firm* — Adam K. Sacharoff

(57) ABSTRACT

In one embodiment there is provided a system for light therapy. The system includes a light guide transmission device having at least one UV bulb for dispersing UV light a light guide cable to a light guide terminating end, an optical capturing device operable to receive an image from a lens positioned at an optical cable terminating end, and a fluid delivery/suction device along a flexible hose. Each of the cables being inserted into a probe cable having a tip adapted for use internally or externally with a patient. Further the system includes a single controller in communication with and for controlling the functionality of the light guide transmission device, the optical capturing device, and the fluid delivery/suction device.

3 Claims, 4 Drawing Sheets

METHOD AND APPARATUS FOR THE COMBINED APPLICATION OF LIGHT THERAPY, OPTIC DIAGNOSIS, AND FLUID TO TISSUE

CROSS REFERENCE TO RELATED APPLICATIONS

The present invention is a Continuation In Part of U.S. application Ser. No. 11/363,554 filed Feb. 27, 2006.

FIELD OF THE INVENTION

The present invention relates to a method and apparatus for the combined application of light therapy, optic diagnosis, and fluid to tissue and blood and can further relate to a method and apparatus for irradiation, phototherapy, and irrigation of fluid to the mucous and/or tumor cites.

BACKGROUND OF THE PRIOR ART

Ultraviolet (UV) light can be used to treat a multitude of medical problems, including for example bacterial, viral and fungal infections, poisoning, fatigue, Alzheimer's disease, allergies and asthma, rheumatic diseases and arthritis, diabetes, hepatitis, and cancer. The treatment relates to the fact that UV light tends to sterilize the blood and act as an antibiotic.

In UV light therapy, a treatment provider generally illuminates the patient's skin or blood. If the UV light is applied to the skin it is typically provided to the patient's skin either with a wrap or lamp. Applying. the UV light directly to a patient's blood supply is known as photoluminescence or UV blood illumination (UBI). UV blood illumination increases oxygen, destroys toxins and boosts the immune system. In prior art UBI, a small amount of blood is drawn from the patient, up to about 250 cc. The body has about 5.6 L of blood. The blood that is drawn travels through a cuvette or glass chamber. The blood is repeatedly illuminated with UV light and then returned to the body. The process is repeated, typically a day or several days later. These treatments are time consuming, and require regular trips to a medical facility. In addition, trained personal must be available to provide the treatments.

There is a need for alternative treatment methods and apparatus that is adapted for various different therapies and treatments.

SUMMARY OF THE INVENTION

In one embodiment of the present invention there is provided a system for light therapy. The system includes a light guide transmission device, an optical capturing device, and a fluid delivery/suction device. A single controller is in communication with and operable for controlling the functionality of the light guide transmission device, the optical capturing device, and the fluid delivery/suction device.

The light guide transmission device has at least one UV bulb for dispersing UV light at a predetermined therapeutic wavelength. The UV bulb is preferred to be encased in a protective casing, which may be an opaque casing. A portion of the casing is opened to connect to one end of a light guide cable such that the UV light is channeled into and through the light guide cable to a light guide terminating end. The optical capturing device is operable to receive an image from a lens positioned at an optical cable terminating end defined from an optical cable extending from the optical capturing device. And the fluid delivery/suction device having a pump and a generator for pumping and suctioning a fluid along a flexible hose and out the end of the flexible hose.

The system may further be defined to include two UV bulbs. Each bulb is encased in an opaque protective casing and has separate opened portions, each of which being connected to an branches of a light guide cable. The two branches having a joining region to form into the light guide cable with the light guide terminating end.

In other embodiments, the fluid delivery/suction device includes a pair of tanks. A first tank for supplying the fluid to the flexible hose during pumping and a second tank for receiving the fluid when suctioning fluid through the flexible hose.

In addition, the system would include a probe cable having a tip adapted for use internally or externally with a patient. The tip encases a terminating end of the probe cable. The probe cable also has an opening to receive the light guide cable, the optical cable, and the flexible hose. Preferably, the probe cable has a predetermined length such that the light guide terminating end, the end of the flexible hose and the lens from the optical cable all terminate at the tip of the probe cable. In other aspects, the tip of the probe cable includes a cover, which has at least one aperture to accommodate the end of the flexible hose from the fluid delivery/suction device.

Numerous advantages and features of the invention will become readily apparent from the following detailed description of the invention and the embodiments thereof, and from the accompanying drawings.

BRIEF DESCRIPTION OF THE DRAWINGS

A fuller understanding of the foregoing may be had by reference to the accompanying drawings, wherein.

DETAILED DESCRIPTION OF THE INVENTION

Figure 1:
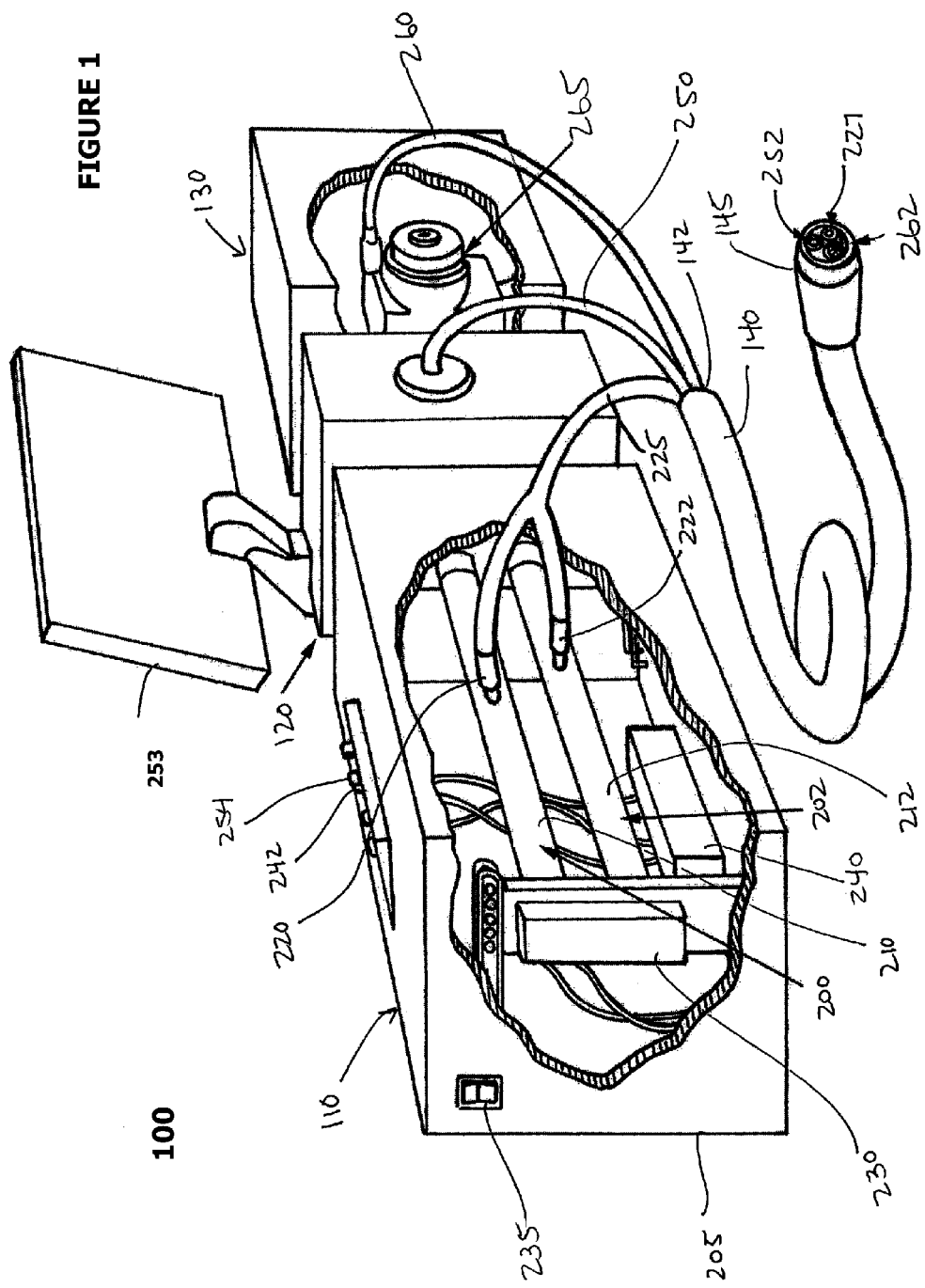
FIG. 1 is a top view of a system diagram of a multi-frequency light guide transmission therapy assembly having light treatment therapy, optical capturing, and water delivery/suction capabilities.

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the claims by the embodiments illustrated.

Light at one or more therapeutic wavelengths such as ultraviolet light (UV), is used to treat many diseases including infections, poisoning, fatigue, allergies, hepatitis, cancer and HIV. UV light increases the oxygen combining power of the blood, destroys toxins, viruses, fungi, bacteria, and boosts the immune system. UV light also sterilizes and acts as an antibiotic.

Preferably, UV light at one or more therapeutic wavelength is utilized in the present invention. More preferably either UV-A or UV-C light or a combination of UV-A and UV-C light is utilized in the present invention. For some conditions and/or diseases UV-A light is more effective than UV-C and for other conditions and/or diseases UV-C light is more effective than UV-A light. The wavelengths or wavelengths of light to be used to treat the patient are selected based on the wavelength or wavelength that will best treat the condition or disease of the patient. Optionally, the device also utilizes infrared light. IR irradiation prepares the tissue to absorb more of the therapeutic UV light.

Figure 2:
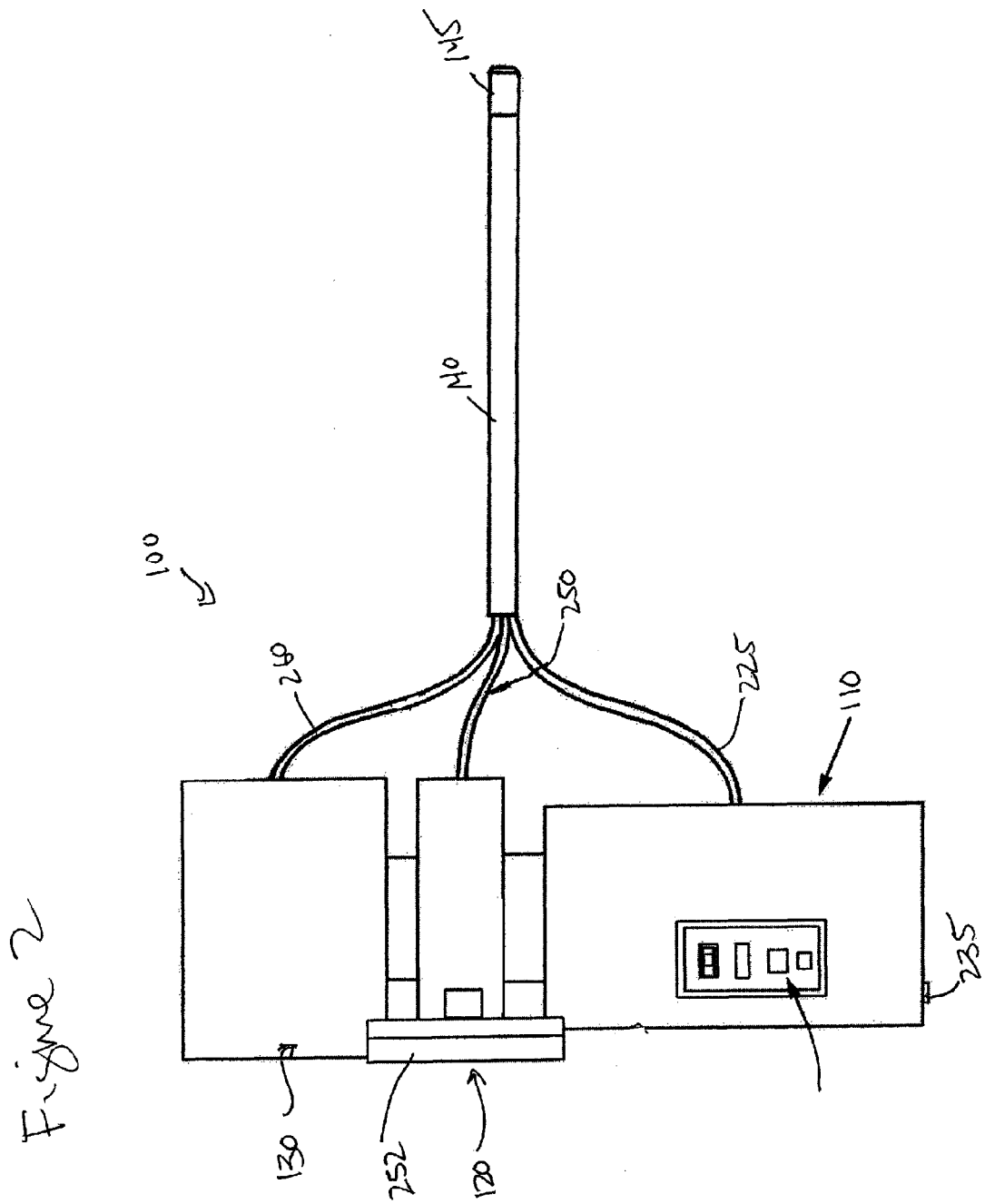
FIG. 2 is a partial section side view of FIG. 1.
Figure 3:
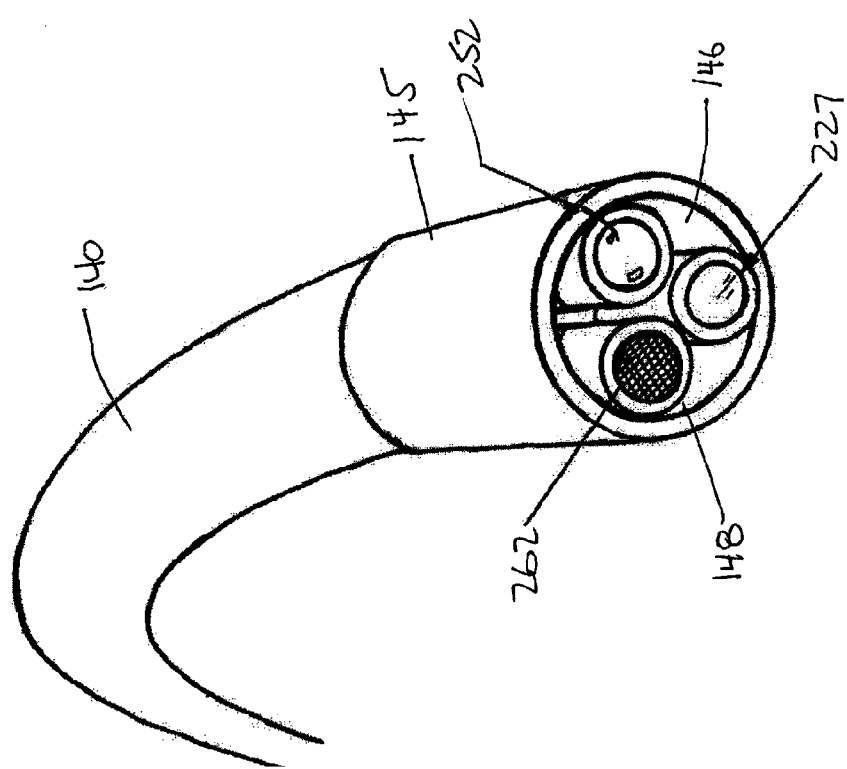
FIG. 3 is a multi-frequency light guide transmission therapy cable assembly having optical capturing and water delivery/suction capabilities.
Figure 4:
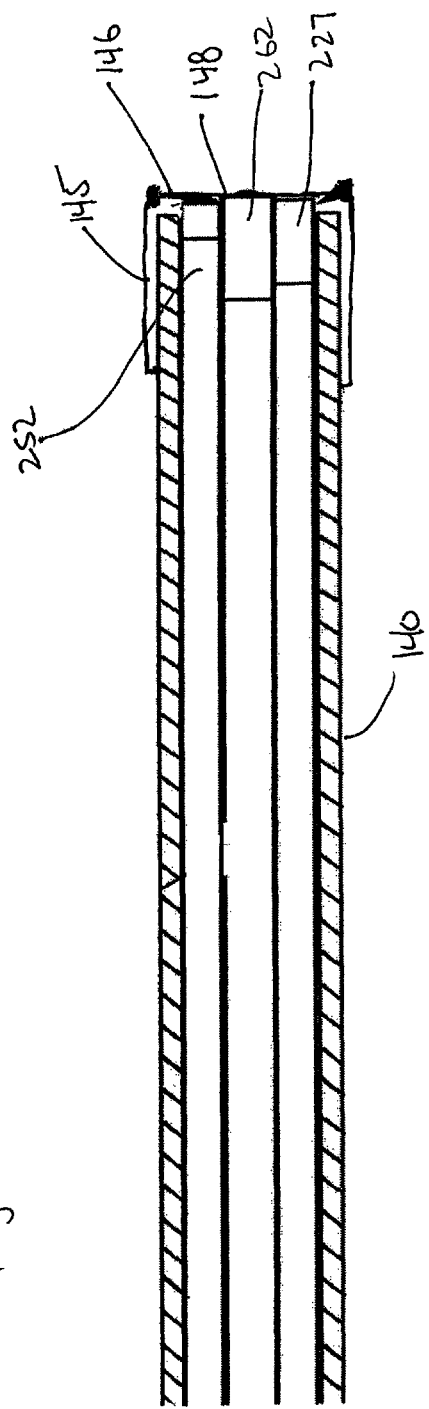
FIG. 4 is a sectional view of the therapy cable from FIG. 3.

Referring now to FIGS. 1 through 4, there is illustrated, a system 100 for a multi-frequency light guide transmission therapy assembly having a light treatment therapy, an optical capturing capability, and a water delivery/suction capability. The system would connect and control a light guide transmission device 110, an optical capturing device 120, and a fluid delivery/suction device 130. Each device would communicate through separate cables that would travel through a probe cable 140. The probe cable 140 terminating at a tip 145, all of which can be used for the treatment of a patient.

In more detail, the light guide transmission device 110 would have multiple UV bulbs 200 and 202 for dispersing UV light along various wavelengths, such as, UVA and UVB. The bulbs would be housed in the light guide transmission housing 205. Each bulb would be separately encased in a UV protective casing 210 and 212, the light from each would be channeled into separate ends 220 and 222 of a light guide cable 225. The ends 220 and 222 of the light guide cable 225 could form a y-shape continuous feed.

The light guide cable 225 is then feed into a first end 142 of the probe cable 140. The light guide cable 225 would terminate at a light guide end 227 positioned at the tip 145 of the probe cable 140.

Still referring to the light guide transmission device 110, the device 110 is used to illuminate a portion of the patient with therapeutic UV wavelength(s). The UV light illuminates the patient's skin, mucous membrane, blood, organ, tumor or other tissue. The device comprises a power supply 230 to supply power to one or more of the bulbs. The light guide cable 225 comprises a light guide tip 227 that emits the UV light, the light may be any therapeutic wavelength(s) such as UV-A and/or UV-C. Alternatively, the emitted light may also be IR, visible light, or any combination of desired wavelengths.

The light guide transmission device 110 transports the therapeutic wavelength(s) of light to directly to the blood, organ, mucous membrane, tumor, or other tissue. Thus, infected or damaged tissue or tumor can be directly treated. For example, the digestive tract is coated with mucous membrane and us when the flexible tube is inserted through the mouth or anus, sensitive capillaries can be a radiated. Capillary exposure of the mucous membrane is significantly greater than other externally exposed body surfaces. Greater capillary exposure allows for greater penetration of the therapeutic ultraviolet spectrum.

In one embodiment, the light guide cable 225 is a liquid core light guide or other known light guide. In one embodiment, the light guide is made of rubber or other flexible tubing and houses fiber optic strands. Optionally the light source could be a cold cathode fluorescent bulb.

The light guide transmission device 110 could further be turned on and off manually by a side switch 235. Alternatively, device 110 could automatically turn off one or more of the bulbs at selected treatment times or durations. Further, the light source could automatically be turned off after a set treatment duration, such as twenty minutes.

The system 100 further includes an optical capturing device 120. The optical capturing device is used to view, capture, and process images of tissue or other affective areas being treated. The optical capturing device would in most cases be designed and developed to mimic well known endoscopy devices such that it would include a flexible tube or cable 250 with a lens 252 at an end thereof. The flexible cable 250 is feed through the probe cable 140 such that the lens 252 would terminate at the tip 145. The optical capturing device 120 would further include a monitor 253 and controls 254.

The system 100 yet still further includes a fluid delivery/suction device 130. The fluid may be preferably water, but it does not have to be limited to such. The fluid device 130 would include a flexible hose 260 and having an end 262. The flexible hose 260 would be feed through the flexible cable 140 such that the end 262 would terminate at the tip 145 of the flexible cable 140. The fluid delivery/suction device 130 would include a generator and a pump assembly 265 and may include a pair of tanks, one for delivering the fluid to the end of the flexible hose 260 and one for emptying the fluid when suctioning fluid. This would help prevent contamination of fluid and allow the treatment to have clean and even sanitary fluid when delivering the fluid to the treatment area.

The tip 145 of the flexible cable 250 may include a cover or lens 146 that protects the cable(s). The lens 146 has an apertures 148 sized to receive the end 262 of the flexible hose 260 from the fluid delivery/suction device 130. This helps protect the probe cable housing 140 and prevents back flow of liquids and debris. Preferably, the tip is made of a transparent material or other material that allows emission of UV light. Optionally, the tip has a window the permits the emission of the UV radiation. Preferably, the tip is made of a non-rigid, semi-flexible or flexible material as this will be more comfortable for the patient. The tip 145 may be secured to the flexible cable 250 by an epoxy sealer or other sealant to keep bodily fluids from getting into flexible cable 250.

The probe cable 140 is preferably made of rubber or other non-rigid medical grade material. Preferably, the material is flexible so that tubing can be inserted into an orifice of the patient, such as the nose, ear, mouth, vagina or rectum and then with the aid of a camera threaded until the tip is directed at the selected tissue. Alternatively, a portion of the probe cable 140 is inserted into the patient and the tissue treated laproscopically. In another alternative, patient has a port and is surgically implanted and tubing and tip are inserted through the port. In yet another alternative, a portion of probe cable 140 can be surgically implanted in patient.

The system 100 would further be provided and programmed with a control system 240 that would have an input center 242 accessible by a treatment provider to control the light sources, duration times, optical device and the fluid delivery and section device as well as other treatment aspects. The control system such as a computer or other smart interface could be programmed to limit the number of treatments given in a time period, limit the total amount of treatment time in a given time period, automatically provide treatments, pulse the light source(s), and/or alternate between selected therapeutic wavelengths or between ultraviolet and infrared wavelengths or provides only particular wavelengths. The control system could keep a treatment records and/or could communicate wirelessly, via the Internet or through other electronic means to automatically update the doctor's treatment records. The control system preferably can automatically adjust treatment time, wavelength or other factors based on patient input, doctor orders or other data.

The treatment provider during treatment would be able to insert the tip 145 into a patient when a treatment is needed. The treatment provider would be capable of viewing images provided by the optical device on a monitor. The treatment provider would then be able to use the images to identify tissue to be sampled, biopsied or to receive treatment. The images allow the treatment provider to identify the tissue and to position the light guide. Preferably the selected tissue is first a radiated with infrared light. Then the selected tissue is a radiated with one or more therapeutic wavelengths such as UVA, UVC or a combination of UVA and UVC light. During treatment the fluid delivery/suction device could be used by the treatment provider to supply fluid to the area in a better view needs to be obtained or to clear blood or other bodily fluids from the area. Similarly the suction can be used to help remove the blood, fluids, etc. from the area.

From the foregoing and as mentioned above, it will be observed that numerous variations and modifications may be effected without departing from the spirit and scope of the novel concept of the invention. It is to be understood that no limitation with respect to the specific methods and apparatus illustrated herein is intended or should be inferred.

I claim:

1. A system for light therapy comprising:
   a light guide transmission device having a light guide determining end, at least one UV bulb configured to disperse UV light at a predetermined therapeutic wavelength, the at least one UV bulb being encased in an opaque protective casing with a portion of the casing being opened to connect to one end of a first light guide cable section, and an infrared light source encased in an opaque protective casing with a portion of the casing being opened to connect to one end of a second light guide cable section, and wherein the second light guide cable section and the first light guide cable section being connected at a joining region, the joining region being further configured to connect to the light guide transmission device, such that the UV light and the infrared light is channeled into and through a single light guide cable to a light guide terminating end;
   an optical capturing device operable to receive an image from a lens positioned at an optical cable terminating end defined from an optical cable extending from the optical capturing device;
   a fluid delivery/suction device having a pump and a generator for pumping and suctioning a fluid along a flexible hose and out the end of the flexible hose;
   a probe cable having a tip adapted for use internally or externally with a patient, the tip encasing a terminating end of the probe cable, the probe cable having an opening to receive the light guide cable, the optical cable, and the flexible hose, the probe cable having a predetermined length such that the light guide terminating end, the end of the flexible hose and the lens from the optical cable all terminate at the tip of the probe cable; and
   a single controller in communication with and for controlling the functionality of the light guide transmission device, the optical capturing device, and the fluid delivery/suction device, and the single controller being configured with programming instructions to initiate the infrared light prior to the initiation of the UV light to prepare tissue being exposed to the light guide transmission device to better absorb UV light.

2. The system of claim 1, wherein the fluid delivery/suction device includes a pair of tanks, a first tank for supplying the fluid to the flexible hose during pumping and a second tank for receiving the fluid when suctioning fluid through the flexible hose.

3. The system of claim 1, wherein the tip of the probe cable includes a cover, the cover having at least one aperture to accommodate the end of the flexible hose from the fluid delivery/suction device.

* * * * *